United States Patent [19]
Roshdy et al.

[11] Patent Number: 5,487,469
[45] Date of Patent: Jan. 30, 1996

[54] PACKAGE FOR ENDOSCOPIC INSTRUMENT

[75] Inventors: Constance Roshdy, New Egypt, N.J.; E. Paul Johnson, San Angelo, Tex.

[73] Assignee: Ethicon, Inc., Somerville, N.J.

[21] Appl. No.: 187,274

[22] Filed: Jan. 25, 1994

[51] Int. Cl.$^6$ ................................................. B65D 85/20
[52] U.S. Cl. ........................ 206/363; 206/63.3; 206/476
[58] Field of Search ................................ 206/63.3, 227, 206/363, 364, 380, 438, 477, 476

[56] References Cited

U.S. PATENT DOCUMENTS

| | | | |
|---|---|---|---|
| 4,887,710 | 12/1989 | Roshdy et al. | 206/63.3 |
| 5,101,968 | 4/1992 | Henderson et al. | 206/63.3 |
| 5,199,561 | 4/1993 | Roshdy et al. | 206/63.3 |
| 5,226,535 | 7/1993 | Roshdy et al. | 206/364 |
| 5,358,624 | 10/1994 | Roshdy et al. | 206/364 |

*Primary Examiner*—Jimmy G. Foster
*Attorney, Agent, or Firm*—Emil Richard Skula

[57] ABSTRACT

A foldable package for an endoscopic suturing device is disclosed. The package comprises a base panel having opposed major sides and opposed minor sides. First and second package closure panels are mounted to one major side, while a mounting panel is mounted to the other major side. A retention panel is foldably connected to the mounting panel. Top and bottom tabs secure the suturing device. An optional needle park is mounted to the mounting panel.

8 Claims, 4 Drawing Sheets

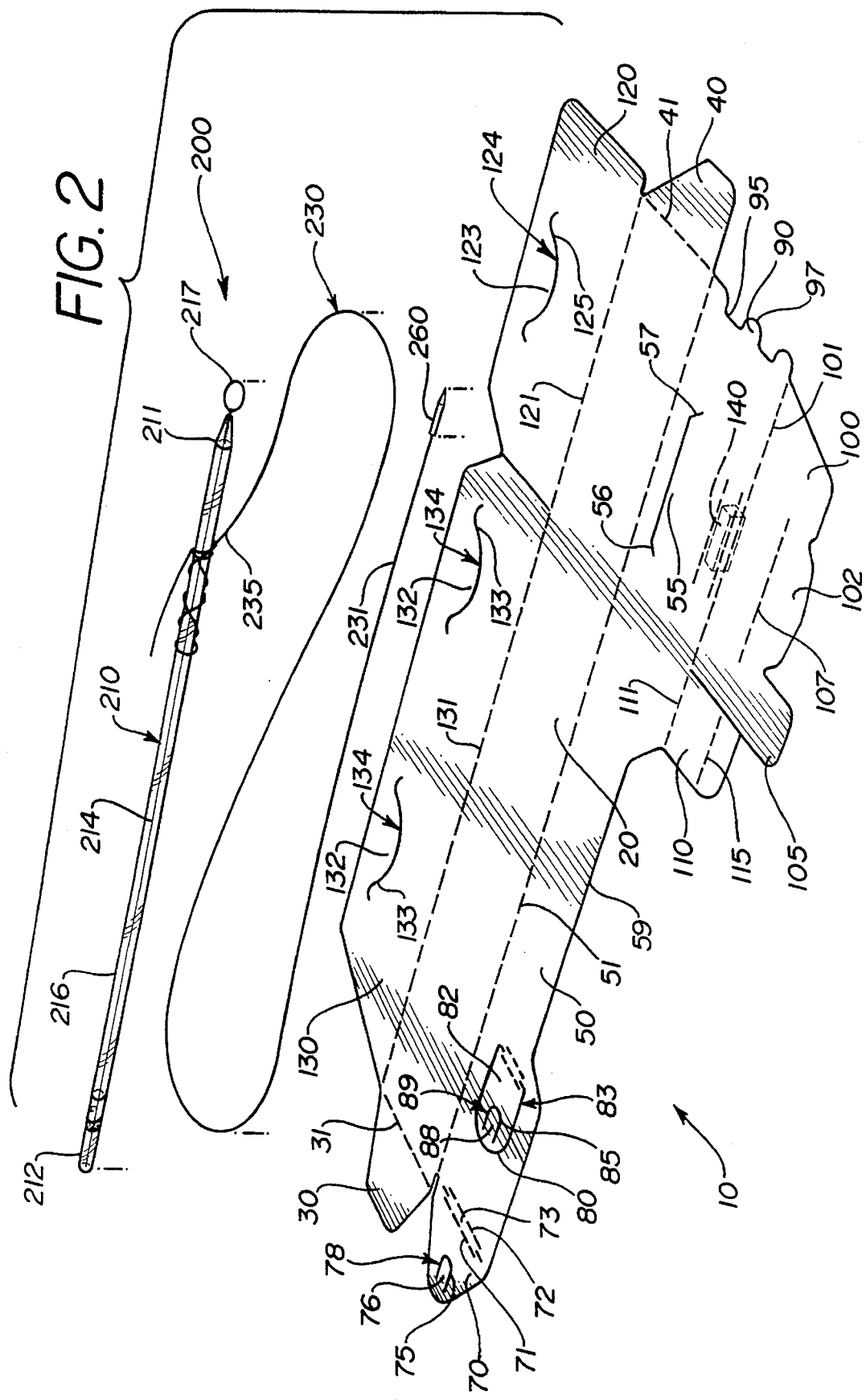

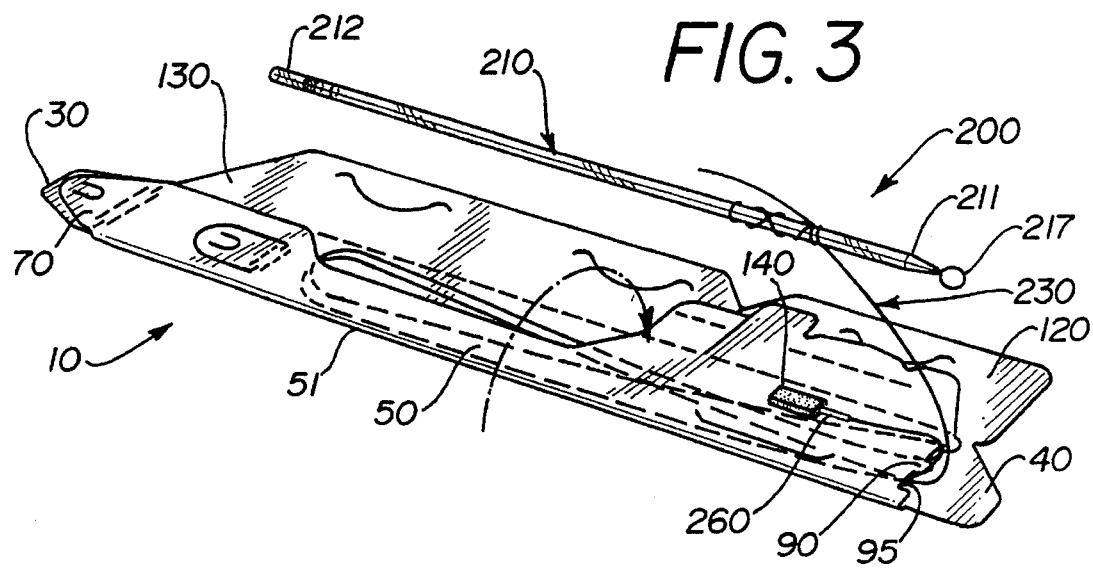
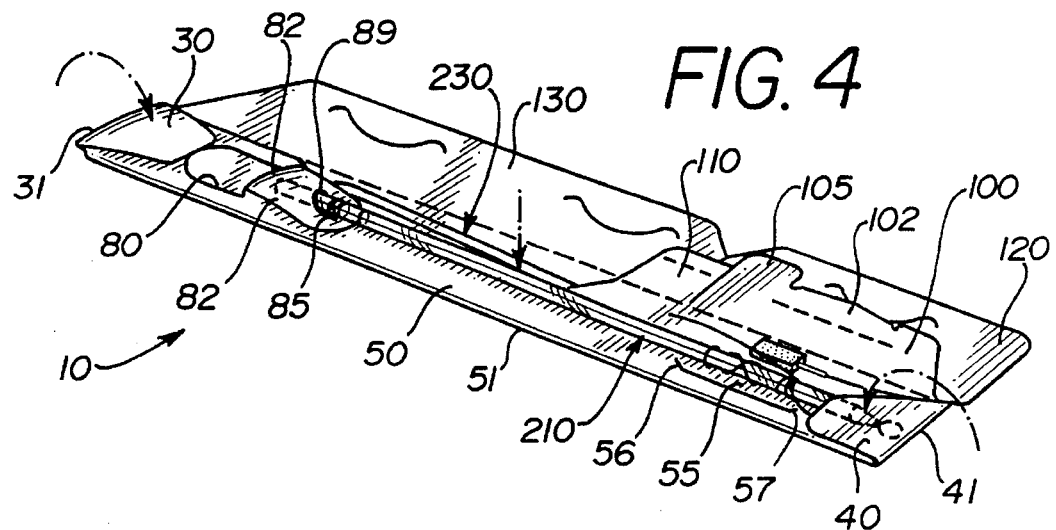
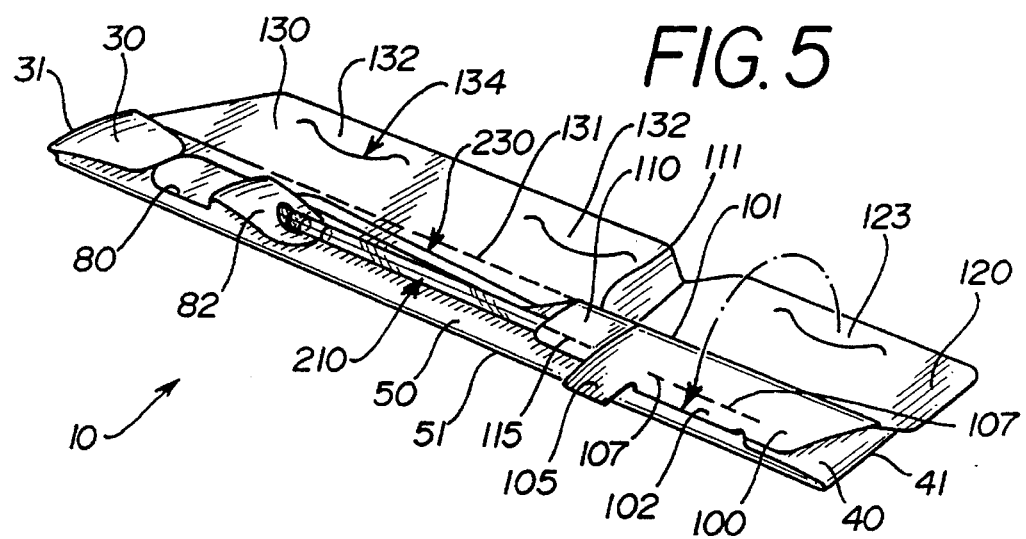

PACKAGE FOR ENDOSCOPIC INSTRUMENT

TECHNICAL FIELD

The field of art to which this invention relates is packaging, in particular, packaging for endoscopic suture devices.

Background of the Invention

Endoscopic surgical techniques (defined herein to include laparoscopic, thoracoscopic and arthroscopic) are becoming widely accepted by the medical profession. The utilization of endoscopic surgical procedures has eliminated the need for radical incisions into the fascia and musculature of a patient in order to access a particular internal part of the patient's body. In a typical endoscopic procedure, trocars are typically inserted into the body to penetrate through to body cavities, such as the abdominal cavity. The trocars typically consist of two primary components, the first of which is an elongated piercing instrument, known as an obturator. The trocar assembly also contains a trocar cannula in which the trocar obturator is housed. The trocar cannula remains in the body cavity after the trocar obturator is removed and serves as a pathway to and from the body cavity.

Various types of endoscopic instruments may be inserted through the trocar cannula pathway, including endoscopes, stapling apparatuses, cutting and ligating apparatuses, and the like. As in most surgical procedures, it is frequently necessary to suture various tissue sites within the body which are the subject of an endoscopic surgical procedure. Accordingly, various types of endoscopic suture devices such as suture and cannula assemblies have been developed to satisfy this need.

It is essential that the endoscopic suture devices be packaged in such a manner that the devices are protected during shipping, handling, and, of course, during sterilization procedures. Many conventional sutures tend to have memories due to the nature of the materials from which they are made. A suture made from such a suture material, which becomes shifted in its package during sterilization, shipping, handling, etc., will typically tend to retain a resulting distorted shape, possibly making the suture device unusable for an endoscopic surgical procedure. In addition, it is important that the endoscopic suture device be easily removable from a package in an operating room without damaging the suture and cannula or compromising its sterility. In addition, since a packaged endoscopic suture device is typically placed into a plastic overwrap envelope prior to sterilization, it is critical that the plastic overwrap be protected from the cannula to prevent punctures and tears. Once the plastic overwrap is punctured or torn, the sterility of the endoscopic device is compromised and the device must typically be disposed of since it cannot be resterilized in a hospital environment.

What is needed in this art are packages for endoscopic suture devices which are easy and economical to manufacture and which protect the devices during shipping, sterilization and handling and which further prevent the devices from shifting in the package.

Summary of the Invention

It is an object of the present invention to provide a package for an endoscopic suture device which protects the cannula and suture during sterilization, handling, shipping and storage, but which allows the device to be easily removed in an operating room.

It is a further object of the present invention to provide a package which maintains the suture of an endoscopic suture device in a substantially fixed position within the package.

It is yet another object of the present invention to provide a package for an endoscopic suture device which minimizes the possibility of tears or punctures to a plastic outer wrap.

It is a further object of the present invention to provide such a package which is easy and economical to manufacture.

Accordingly, a foldable package for an endoscopic suture device is disclosed. The package comprises a base panel. The base panel has a pair of opposed major sides and a pair of opposed minor sides. A top tab is foldably connected to the top minor side of the base panel and a bottom tab is foldably connected to the bottom minor side of the base panel. A first closure panel is foldably connected to one major side of the central panel along the upper portion of that side. A second package closure panel is foldably connected to the same major side of the base panel immediately below the first closure panel. A mounting panel is foldably connected to the other major side of the base panel and is disposed substantially opposite to the closure panels. The mounting panel has an optional recessed section along one major side. A suture retaining tab extends from one end of the mounting panel. A retention panel is foldably connected to the mounting panel. A pull tab extends from the retention panel. A stability tab is foldably connected to the mounting panel immediately below the retention panel. The package has means for locking the cannula within the package and means for locking the closure panels. The cannula locking means optionally comprise a U-shaped slot in the proximal tab for receiving and engaging the bottom end of the cannula, and, a U-shaped slot and at least one tab in the suture retaining panel for engaging the distal end of the cannula. The closure panel locking means comprises tabs and tab pockets in the closure panels. The tabs and tab pockets of the closure panels receive and engage the base panel and mounting panel the fold line between the base panel and the mounting panel.

Other features and advantages of the invention will become more apparent from the following description and accompanying drawings.

BRIEF DESCRIPTION OF THE DRAWINGS

FIG. 2 is a perspective view of an endoscopic suture device, and, the package of the present invention prior to assembly.

FIGS. 3–6 are perspective views of the assembly of the package of the present invention.

DESCRIPTION OF THE PREFERRED EMBODIMENTS

Figure 1:
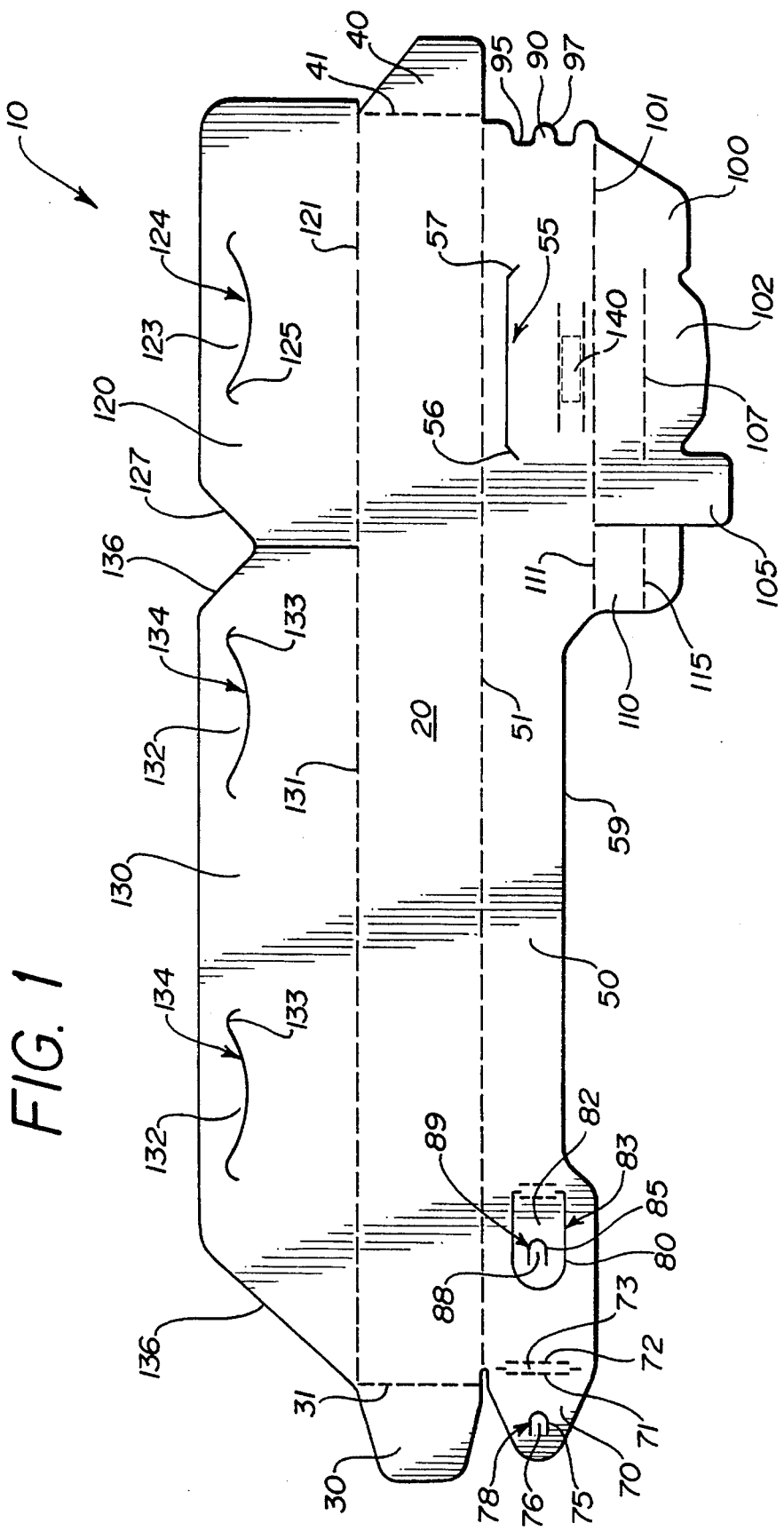
FIG. 1 is a plan view of the package of the present invention prior to folding.
Figure 6:
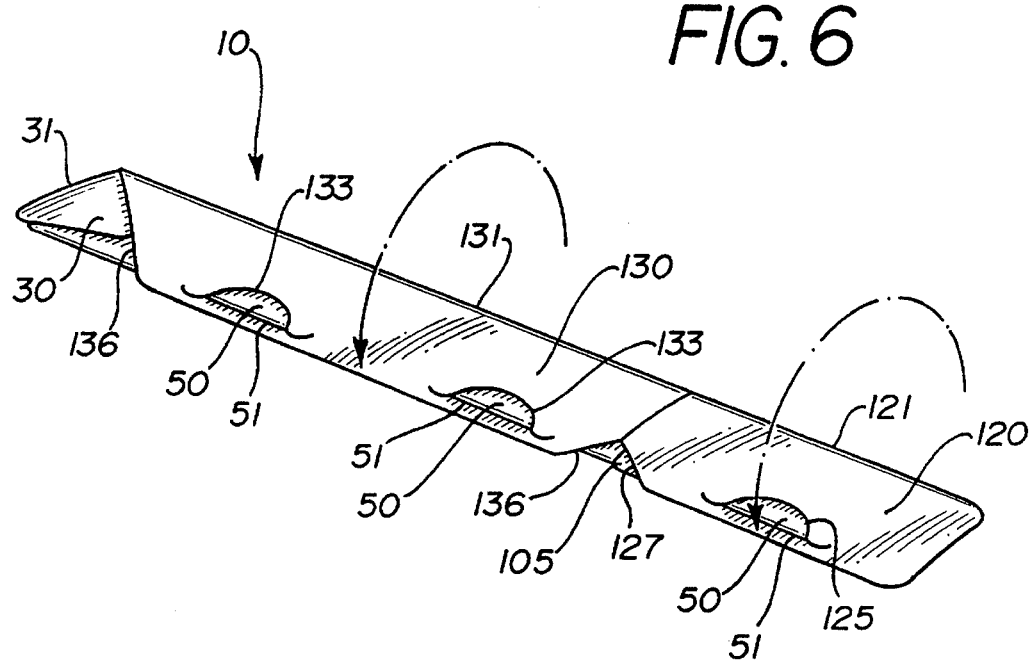

Referring to FIG. 1 and FIG. 2., the package 10 of the present invention is seen to have an inner side and an outer side. The package 10 has base panel 20. The base panel 20 is typically rectangularly shaped having a pair of substantially opposed major sides and a pair of substantially opposed minor sides. It will be appreciated by those skilled in the art that the base panel 20, as well as other panels of the package 10, may have other geometric configurations, for example, curved or sloping major sides. At the lower minor side of the base panel 20 is located bottom tab 30 which is foldably connected to the central floor panel 20 along fold line 31. At the top minor side of the base panel 20 is tab 40 foldably connected to base panel 20 along fold line 41.

Foldably connected to a first major side of the base panel 20 along fold line 51 is the mounting panel 50. The mounting panel 50 is seen to be substantially rectangularly shaped and is further seen to have a pair of opposed major sides and a pair of opposed minor sides. Along the major side opposite to fold line 51, the mounting panel 50 is seen to have tab section 55 and tab pocket 57 formed by slit 56. Along the second major side of the mounting panel 50 is the optional recessed section 59 formed by cutting out a portion of panel 50 along the second major side. Recessed section 59 may contribute to relieving pressure on the suture 230 thereby making it easier to withdraw suture 230 from package 10. Located at the bottom major side of panel 50 is the tab member 70. Tab member 70 is foldably connected to panel 50 along fold lines 71 and 72. Fold lines 71 and 72, which are coextensive in part, form optional gusset member 73. If desired, a single fold line can be used to connect tab member 70 to mounting panel 50. Tab member 70 is seen to have U-shaped slit 75 forming tab 76 and opening 78. The mounting panel 50 is seen to have U-shaped slit 80 forming tab 82 and opening 83. The tab 82 is seen to have U-shaped slit 85 forming tab 88 and cannula receiving hole 89. Extending centrally from the top minor side of panel 50 is the tab member 90 having U-shaped spaces 95 along either side. Tab member 90 is seen to have blunt rounded nose section 97.

Foldably connected to the top, opposite major side of panel 50 along fold line 101 is the retention panel 100. The retention panel 100 is an irregularly shaped panel having tab member 102 extending from the side opposite to fold line 101. The pull tab 105 is seen to extend immediately below tab member 102. Panel 100 is seen to have optional, partial central fold line 107. The stability tab 110 is seen to be foldably mounted to panel 50 immediately below retention panel 100 along fold line 111. Stability tab 110 is seen to have optional central fold line 115.

Foldably connected to the other major side of base panel 20 along fold line 121 is the upper closure panel 120. Panel 120 is substantially rectangular is shape having a pair of opposed major sides and a pair of opposed minor sides. Panel 120 is seen to have tab 123 and tab pocket 124 formed by slit 125. Panel 120 is seen to have optional angulated corner 127. Foldably connected to base panel 20 along fold line 131 and located below upper closure panel 130 is the lower closure panel 130. Panel 130 is seen to have tabs 132 and tab pockets 133 formed by slits 134. The panel 130 is also seen to have angulated corners 136.

Optional needle park member 140 is seen to be mounted to the outer surface of mounting panel 50. Needle park member 140 is preferably made from a polymeric foam and mounted to the panel 50 using conventional adhesives, fasteners and the like. Other conventional and equivalent needle parks may be used including slits in the panel 50.

Referring to FIG. 2, an endoscopic suturing device 200 which can be packaged in the package 10 of the present invention is illustrated. The device is seen to have a cannula 210 having distal end 211 and proximal end 212. The cannula has central passage 214 containing wire 216. Wire 216 has distal loop 217. Suture 230 is seen to have distal end 231 mounted to the surgical needle 260 and proximal end 235 tied about the distal end of the cannula 210 in a knot precursor configuration.

A preferred technique for assembling the package 10 is illustrated in FIGS. 3–6. In order to assemble package 10, initially the suture is looped about the tab 90 of mounting panel 55 such that the loops of suture 230 rest upon the inner side of the mounting panel 50. Then, the mounting panel 50 and the suture 230 are rotated inwardly such that the suture 230 is resting upon the inner surface of the base panel 20, and, the inner surface of retaining panel 50 is substantially parallel to the inner surface of the base panel 20 and resting upon the suture 230. The needle 260 is then inserted into the needle park member 140 and the cannula 210 is laid upon the outer surface of the mounting panel 50 such that the distal end 211 of the cannula 210 is adjacent to the top of the panel 50 while the proximal end 212 of the cannula 210 is inserted into either hole 89 of tab 82 or hole 78 of tab panel 70. Depending upon the length of the cannula, either tab 82 or tab panel 70 may be used to retain the proximal end 212 of the cannula 210. Tab 82 is used as illustrated in FIG. 4. Next tab 40 is rotated about fold line 41 such that the inner surface of tab 40 is substantially parallel to the outer surface of mounting panel 50. Then, the retention panel 100 is rotated about fold line 101 and tab 102 is inserted into the tab pocket 57. Preferably, panel 100 is sized to produce a "tenting" action about fold line 107. Stability tab 110 is similarly rotated about fold line 111 and the end of tab 110 is partially rotated about fold line 115 to produce a tenting action. Then, tab panel 70 is rotated inwardly about fold line 73. Next tab 30 is rotated inwardly about fold line 31 such that the inner surface of tab 30 is substantially parallel to the inner surface of tab member 70. Next, closure panels 120 and 130 are folded about fold lines 121 and 131, respectively, and the outer surfaces of panels 50 and 20 are partially engaged along fold line 51 in tab pockets 134 and 124, thereby locking the package.

Figure 7:
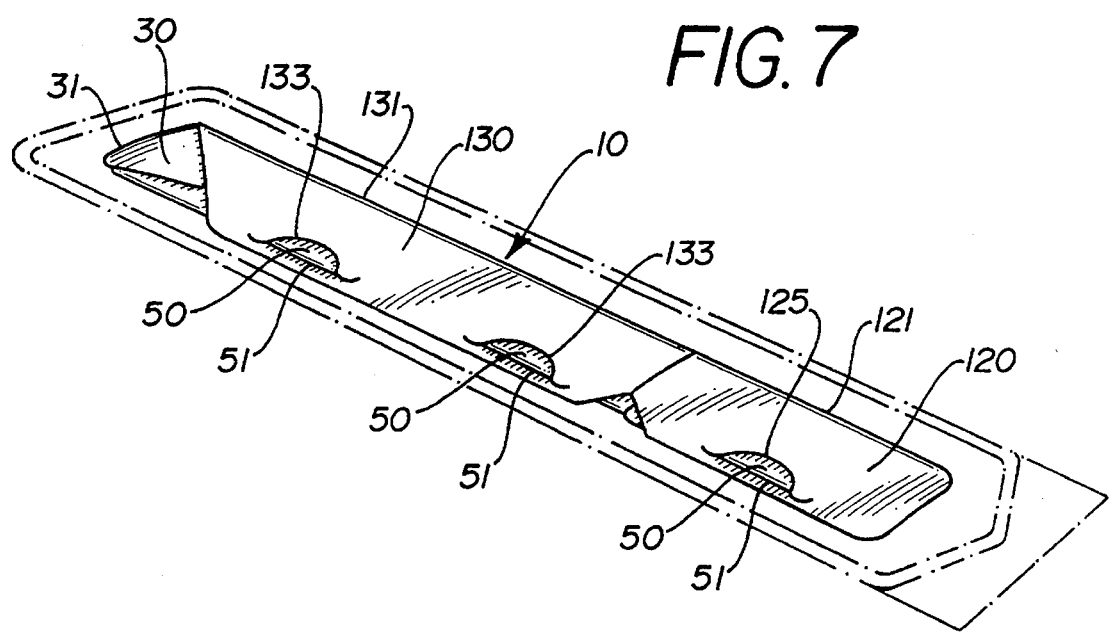
FIG. 7 is a perspective view of an assembled package of the present invention containing an endoscopic suture device.

The assembled package 10 containing the endoscopic suturing device 200 is seen in FIG.7. The package 10 is shown inserted into a conventional plastic envelope 180 indicated by broken lines.

Referring to FIG. 7 and FIGS. 3–6, the package 10 is easily opened by pulling upwardly on tab 105 extending from retaining panel 100 thereby rotating panel 100 about fold line 101, and, by pulling upwardly on panel 130 and rotating it about fold line 131. The device may then be grasped and removed in one continuous motion by grasping cannula 210 and removing it from receiving hole 89 while the suture 230 is withdrawn from its position between panels 50 and 20 and ultimately the needle is pulled out from the needle park 140.

The packages of the present invention may be constructed out of any material which is easily die cut and scored, and easily foldable, and which has sufficient strength and integrity to adequately protect the loop and catheter during sterilization, shipping, handling and storage. Such materials include conventional materials such as medical grade paperboard. It is particularly preferred to use a conventional, stiff paperboard having a thickness of about 0.008" to about 0.016". The paperboard, as previously mentioned, is preferably an appropriate medical grade. Other materials, including plastics, foils, and laminates combined with each other or with paper may also be used. The packages 10 are made using conventional equipment such as die cutting presses.

It will be appreciated by those skilled in the art that the size of the package 10 and the panels will vary in accordance with the size of the particular endoscopic device, e.g., endoscopic suturing device 200. The package 10 and the panels will be of sufficient size to effectively contain a particular endoscopic device such as device 200 illustrated and described herein.

The package 10 of the present invention containing the device 200 is typically further packaged by insertion into a conventional plastic envelope 180 or a conventional foil packet which is then sealed. Such a plastic envelope typically is made from conventional materials such as TYVEK®, paper polyfoil, polyester copolymer, polypropylene copolymer, combinations thereof, and the like.

The packaged medical devices are typically sterilized using conventional sterilization equipment and processes. Examples of the sterilization processes which can be used on the endoscopic loop and suture cannula assemblies 100 packaged in the foldable package 10 of the present invention include conventional sterilization processes such as Co 60, irradiation, ethylene oxide, methylene bromide, and the like.

The one-piece package 10 of the present invention has many advantages. It is easy to manufacture out of conventional materials. The package 10 is extremely easy to assemble. An endoscopic suturing device is retained and protected during sterilization, shipping, and handling. In particular, a suture is maintained in a fixed configuration. The package 10 is easily opened in an operating room environment, and the endoscopic suture device can be easily removed from the package 10 in one continuous motion. The risk of damaging the device during removal from package 10 is substantially reduced. The package 10 additionally prevents a cannula from puncturing or tearing an outer plastic overwrap envelope.

Although this invention has been shown and described with respect to the detailed embodiments thereof, it will be understood by those skilled in the art that various changes and further detail thereof may be made without departing from the spirit and scope of the claimed invention.

What is claimed is:

1. A foldable package for an endoscopic suturing device comprising:

a base panel having a pair of opposed major sides and a pair of opposed minor sides;

a first upper closure panel foldably mounted to the first major side of the base panel;

a second, lower closure panel foldably mounted to the first major side of the base panel below the first closure panel;

a mounting panel having a pair of opposed major sides and a pair of opposed minor sides mounted to the other major side of the base panel along a first major side of the mounting panel;

a retaining panel mounted to the other major side of the mounting panel;

a bottom tab panel foldably mounted to the lower minor side of the base panel;

a top panel extending from the opposite upper minor side of the base panel;

needle park means mounted to the mounting panel;

means for locking the closure panels to the base panel and mounting panel; and, means for locking the retaining panel to the base panel.

2. The package of claim 1 further comprising needle park means mounted to the mounting panel.

3. The package of claim 1 wherein the locking means for the closure panels comprises tab pockets for engaging the base panel and mounting panel.

4. The package of claim 1 additionally comprising a pull tab extending from the retaining panel.

5. The package of claim 4 further comprising a stability tab foldably mounted to the second major side of the mounting panel below the retention panel.

6. The package of claim 1 wherein the mounting panel comprises a recessed section along the second major side.

7. A foldable package for an endoscopic suturing device comprising:

a base panel having a pair of opposed major sides and a pair of opposed minor sides;

a first upper closure panel foldably mounted to the first major side of the base panel;

a second, lower closure panel foldably mounted to the first major side of the base panel below the first closure panel;

a mounting panel having a pair of opposed major sides and a pair of opposed minor sides mounted to the other major side of the base panel along a first major side of the mounting panel;

a retaining panel mounted to the other major side of the mounting panel;

a bottom tab panel foldably mounted to the lower minor side of the base panel;

a top panel extending from the opposite upper minor side of the base panel;

needle park means mounted to the mounting panel;

means for locking the closure panels to the base panel and mounting panel; and means for locking the retaining panel to the base panel comprising a tab extending from the retaining panel and a tab pocket in the mounting panel.

8. A foldable package for an endoscopic suturing device comprising:

a base panel having a pair of opposed major sides and a pair of opposed minor sides;

a first upper closure panel foldably mounted to the first major side of the base panel;

a second, lower closure panel foldably mounted to the first major side of the base panel below the first closure panel;

a mounting panel having a pair of opposed major sides and a pair of opposed minor sides mounted to the other major side of the base panel along a first major side of the mounting panel;

a retaining panel mounted to the other major side of the mounting panel;

a bottom tab panel foldably mounted to the lower minor side of the base panel;

a top panel extending from the opposite upper minor side of the base panel;

needle park means mounted to the mounting panel;

means for locking the closure panels to the base panel and mounting panel wherein the locking means for the closure panels comprises tab pockets for engaging the base panel and mounting panel;

a suture retaining tab extending from a, top minor side of the mounting panel;

a pull tab extending from the retaining panel;

a stability tab foldably mounted to the second major side of the mounting panel below the retention panel; and, means for locking the retaining panel to the base panel comprising a tab extending from the retaining panel and a tab pocket in the mounting panel.

* * * * *

UNITED STATES PATENT AND TRADEMARK OFFICE
CERTIFICATE OF CORRECTION

PATENT NO. : 5,487,469
DATED : January 25, 1994
INVENTOR(S) : Constance Roshdy
E. Paul Johnson It is certified that error appears in the above-indentified patent and that said Letters Patent is hereby corrected as shown below:

On the title page, item [22],

Filed Date: Should Read January 26, 1994

Signed and Sealed this

Thirteenth Day of August, 1996

*Attest:*

BRUCE LEHMAN

*Attesting Officer*  *Commissioner of Patents and Trademarks*